United States Patent
Mor

[19]

[11] Patent Number: 5,752,294
[45] Date of Patent: May 19, 1998

[54] SYSTEM AND METHOD FOR DETECTION OF COTTON STICKINESS AND NEPS AND OTHER LINT QUALITIES IN REAL TIME AND REMOVAL OF STICKY DEPOSITS FROM PROCESSED COTTON IN THE GIN

[76] Inventor: Uzi Mor, 38. Hshomrin, Rehovot, Israel

[21] Appl. No.: 696,947

[22] PCT Filed: Feb. 22, 1995

[86] PCT No.: PCT/EP95/00647

§ 371 Date: Nov. 7, 1996

§ 102(e) Date: Nov. 7, 1996

[87] PCT Pub. No.: WO95/22762

PCT Pub. Date: Aug. 24, 1995

[30] Foreign Application Priority Data

Feb. 22, 1994 [IL] Israel ........................ 108743

[51] Int. Cl.⁶ .................... G01N 21/00; D01G 31/00
[52] U.S. Cl. .................... 19/66 CC; 250/559.08; 250/559.19; 250/559.4
[58] Field of Search .................... 19/0.21, 66 R, 19/66 CC, 99, 200, 65 R; 73/159, 160; 250/559.11, 559.41, 559.03, 559.01, 559.08, 559.4, 559.45, 559.46; 356/429, 430

[56] References Cited

U.S. PATENT DOCUMENTS

| | | | |
|---|---|---|---|
| 4,969,234 | 11/1990 | Waeber et al. | 19/66 CC |
| 5,003,670 | 4/1991 | Waeber et al. | 19/66 CC |
| 5,130,559 | 7/1992 | Leifeld | 250/562 |

FOREIGN PATENT DOCUMENTS

| | | | |
|---|---|---|---|
| 0344631 | 12/1989 | European Pat. Off. | 19/66 CC |
| 2691545 | 11/1993 | France | 19/66 CC |
| 3928279 | 2/1991 | Germany | 19/66 CC |

*Primary Examiner*—C. D. Crowder
*Assistant Examiner*—Larry D. Worrell, Jr.
*Attorney, Agent, or Firm*—Birch, Stewart, Kolasch & Birch, LLP

[57] ABSTRACT

A system for detection of stickiness, neps, seed coat fragments (S.C.F.) and other fiber qualities comprising (i) an autocleaning microcarding device; (ii) a quality video camera for detection of the number and size of neps, S.C.F. and foreign materials per square unit space and of other qualities of the web; (iii) sticky rollers between which the web is pressed; (iv) a vacuum system pulling said cotton web after pressing; (v) at least one computerized stickiness detector; (vi) means for cleaning the rollers from the sticky lint; (ii) and a computer for processing the obtained data.

15 Claims, 6 Drawing Sheets

5,752,294

SYSTEM AND METHOD FOR DETECTION OF COTTON STICKINESS AND NEPS AND OTHER LINT QUALITIES IN REAL TIME AND REMOVAL OF STICKY DEPOSITS FROM PROCESSED COTTON IN THE GIN

FIELD OF THE INVENTION

The present invention relates to a system for detection and removal of cotton stickiness and detection of other qualities in real time.

Said system has an electro-optic and computerized unit capable of determining the amount of lint sticking to a roller after the carding process.

The present invention relates also to a method for detection of stickiness severity, its adhesiveness, and number of neps and other lint qualities such as length, width, color, and trash seed coat fragments—by the use of said system.

The present invention relates also to a method for separation and removal of sticky deposits which are present in cotton in the course of the ginning process.

BACKGROUND OF THE INVENTION

Sticky trash neps and seed coat fragments (e.g. particles of braked seeds) cotton are serious problems in the cotton industry, as they tend to clog up the spinning machines during its processing at the spinning mills. As a result, the prices of sticky cotton are reduced causing severe losses to the farmer. In some countries (the so called "sticky countries"), the problem is so widespread that cotton prices are reduced by 30–50%.

The main damage caused by stickiness occurs in cotton mills, during the industrial processing of the yarns, where the sticky particles within the raw material clog the rolling parts of the machines, such as pickers, cards or rollers, and as a result tear the cotton yarns. Cotton heavily contaminated by sticky particles primarily tends to clog the pickers, whereas less contaminated cotton tends to clog the cards and especially the spinning rollers. Cotton heavily contaminated by stickiness, neps and seed coat fragments tend to decrease yarn quality and uniformity and increase waste of cotton.

Other qualities such as length, microneer, total amount of trash, lint maturity, percent of lint above 1", are checked by a traditional technique, but needs dramatic improvement, as the new spinning machines are super high speed operated and need very clean and uniform raw cotton. For this purpose, the industry needs a new detecting system which will reliably check, in real time, the traditional qualities.

Several causes have been proposed to explain cotton stickiness, neps and seed coat fragments:

1. Biological, mainly honeydew from whiteflies or aphids, and crushed insects.
2. Physical, namely humidity or static electricity.
3. Physiological, namely a large amount of wax secreted onto the fibres.
4. Industrial or technical, namely oil spilled on the cotton during the ginning process.
5. seed coat fragments can become problem because of weak coat immaturity of the seeds and incorrectly calibrated gining machines.

A partial solution to the stickiness problem would be improving the pest management against honeydew secreting insects. This is done by pest control, as managed by the farmer. This is in the farmer's financial interest to prevent biologically caused stickiness, especially if the percentage of the contaminated bales is low. Today, the whole batch of bales, not only those contaminate, is suspected of stickiness and are reduced in price.

In an attempt to develop a standardization system for sticky cotton, the international market adopted a calorimetric method for determining sugar tests as an indicator for stickiness. This approach was adopted worldwide after several researchers found some correlation between the amount of sugar content in the lint extraction and the degree of stickiness at the mill.

However, the problem remains the low correlation between the stickiness detection and the stickiness at the mill, for it tends to vary between countries and between seasons. In addition, this approach can not provide a constant standard for stickiness, as the small number of bales which are tested are not statistically reliable.

Another approach was to develop mechanical stickiness testers, for detection of stickiness while cotton is run through a similar card process. Three kinds of testers were developed; one simulated the process of the card (hereinafter called "minicard"), the other simulated the process following the pickers, and the third "finds" the honeydew particles after a heating period (hereinafter called "thermodetector"). The advantage of these machines is that they test some kind of stickiness and not indirect detection of sugar content in the cotton. The disadvantage, however, of these three sets of equipment is that they operate very slowly and are not able to detect mass tests for checking all the bales of cotton in real time, as samples from some bales are only passed through the devices. Due to the system's slow operation, in the best cases only two samples from 10–12 bales are tested by minicard. Usually, no minicard tests are done. Another disadvantage is that it lacks a reliable, objective standard for stickiness, as the measure of stickiness is set subjectively by the worker and only the amount of the visible sticky points are measured. The thermodetection systems are also slowly operated and have a potential problem of over detection of non-sticky materials such as the sugars in crushed leaves. Furthermore, the thermodetection system is only useful for honeydew particles contaminated cotton and not for other potential materials for stickiness such as vexes and oils and crushed insects like larvae as described above.

The problem of detecting neps, trash and seed coat fragments remains unsolved. These parameters are very difficult to measure in real time and on the job because of slow operation or absence of technology.

In summary, there is no combined stickiness, neps, trash and seed coat fragments existing system which simultaneously detects stickiness, neps and other qualities in real time, and gives an answer to the real problem of giving a stickiness, trash neps and seed coat fragments number and size, a standard number and reliable quality standards for every bale during the processing in real time.

SUMMARY OF THE INVENTION

The present invention relates to a system for detection of stickiness, neps, trash seed, coat fragments, and other cotton lint quality comprising of an auto cleaning microcarding device for the production of this cotton web; the microcarding device consists of one "lickerin", a main cylinder, 2 carding sites, doffer and takes of cylinder.; a quality video camera for detection of the number and size of neps, trash seed coat fragments per square unit space and for the detection other qualities of the cotton web produced in said auto cleaning microcarding device; stickiness rollers wherein the web is pressed between said rollers; a vacuum system pulling said cotton web and stacking lint after pressing between stickiness rollers; at least one computerized stickiness detector such as laser beam or other illumination source or a camera (C.C.D. camera), said illumination device and its detectors or said camera is connected to a computer for electro-optic checking of the sticky lint on the stickiness rollers; means for automatically re-cleaning the stickiness rollers from the sticky lint; and a computer system for processing the data of sticky lint, and other qualities of the lint exposed by the thin web, and displays them on a screen. Said invention further provides a method for detection of stickiness, neps, trash, and seed coat fragments and lint quality in cotton by the system comprising of the following steps:

(a) automatically or manually "taking" samples of cotton before, during or after the ginning or milling process;

(b) automatically or manually making from the said samples uniform bundles to prepare them for the carding step;

(c) carding said samples to a very thin web of fibers by autocleaning microcarding device for maximum exposure of the sticky deposits, neps, trash, seed coat fragments and other contaminates exsists in said web;

(d) pressing the thin web between rollers and then drawing it by a vacuum system to waste or to packing;

(e) detecting the sticky lint which is stuck to rollers and not drawn, by an illumination beam and its photodetectors, or by at least one camera connected to a computer;

(f) automatic cleaning of the sticky lint form the abovementioned rollers, for preparing the rollers for the next round.

DESCRIPTION OF THE INVENTION

The present invention will be described in detail by FIGS. 1–6. This description clarifies the invention and exemplifies the preferred embodiment but it in no way intends to limit the scope of the invention.

FIG. 1 explains the block diagram of the system according to the present invention.

All other parts are the same.

Figure 4A:
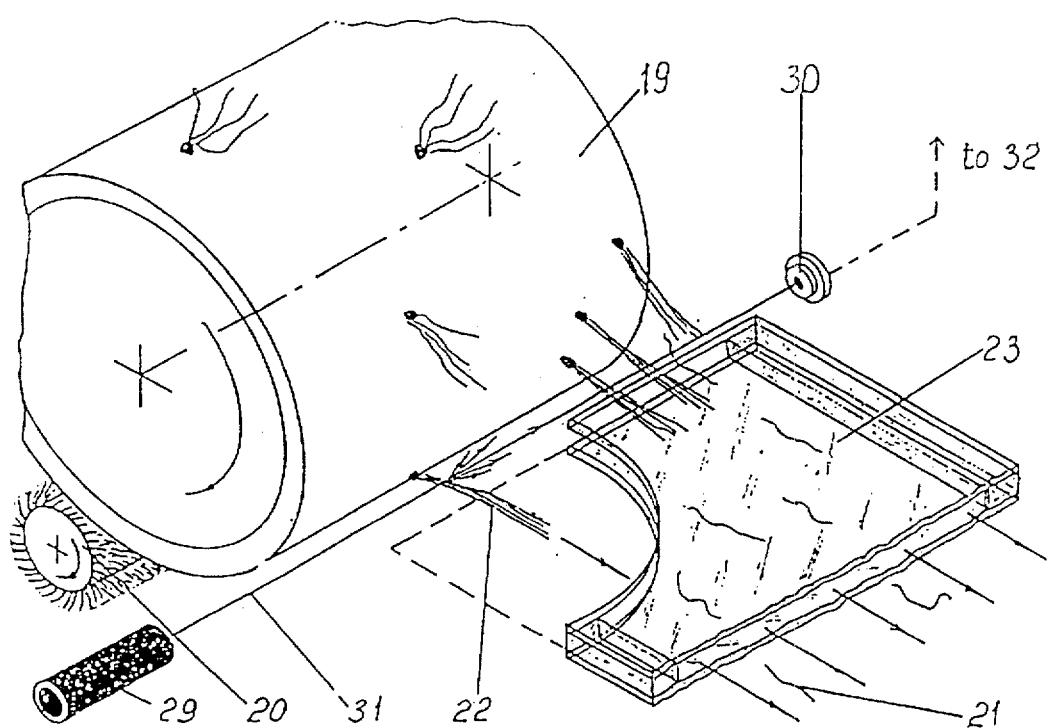
Figure 4B:
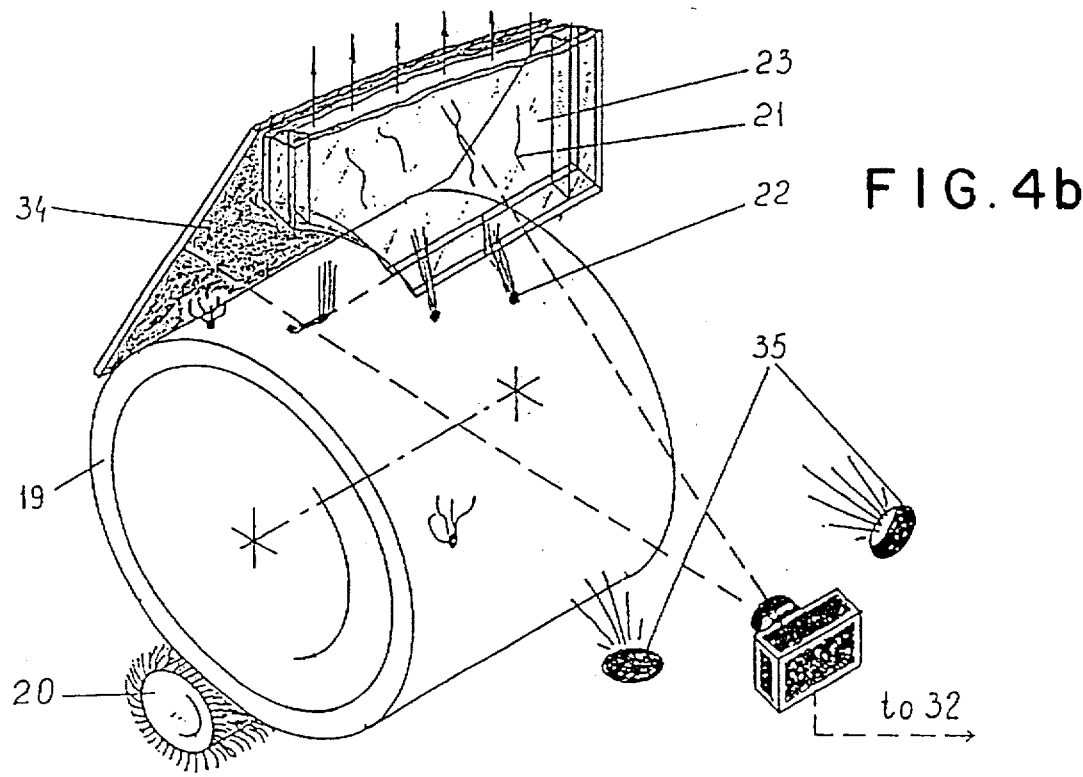

FIG. 4 illustrates a magnified picture of the electro-optic system of the stickiness detector in two versions—one when the system uses illumination and photodetection (FIG. 4a) and the other when a C.C.D. camera is used (FIG. 4b).

Figure 5:
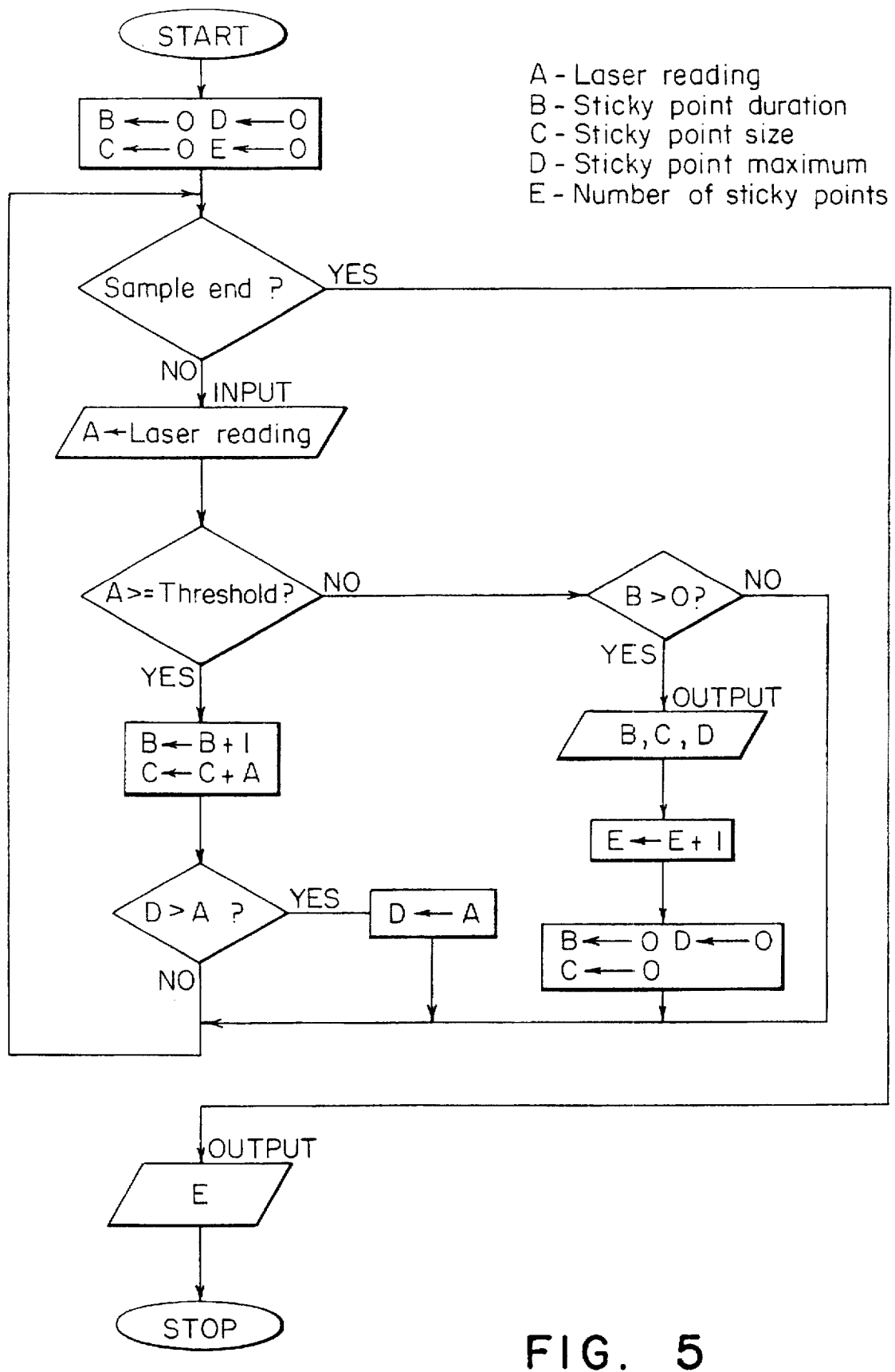

FIG. 5 illustrates the very basic algorithm used for stickiness detection.

Figure 6A:
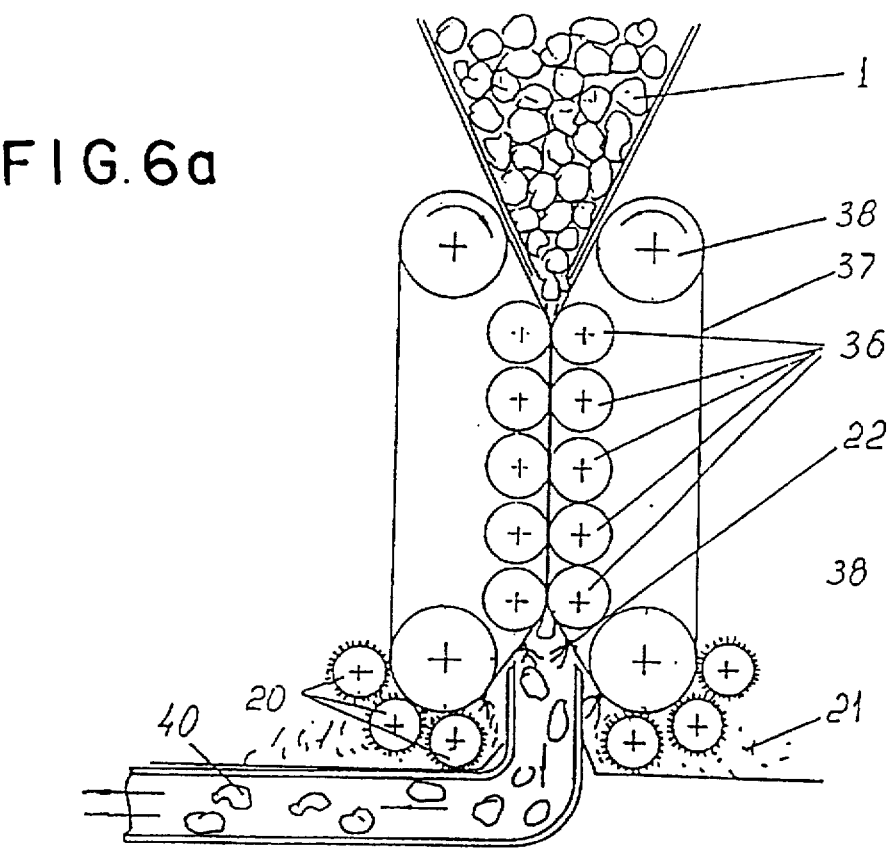
Figure 6B:
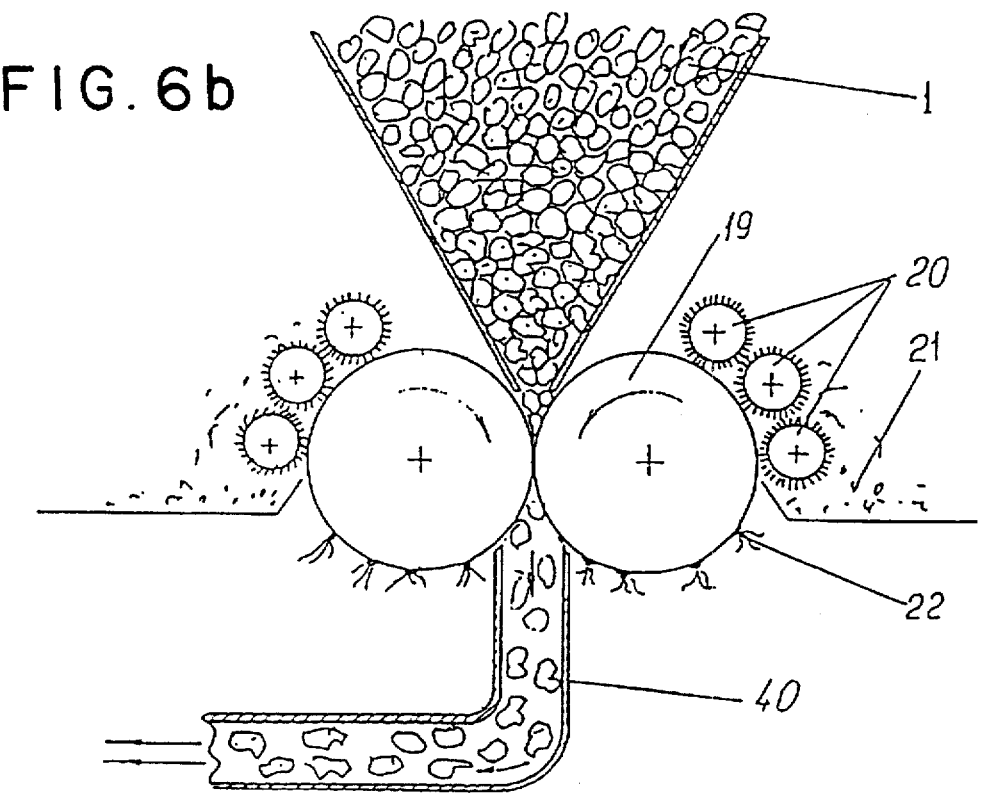

FIGS. 6a and 6b illustrate the same system but with much larger parts for use as a stickiness cleaner at the ginning site.

DETAILED DESCRIPTION OF THE INVENTION

Figure 1:
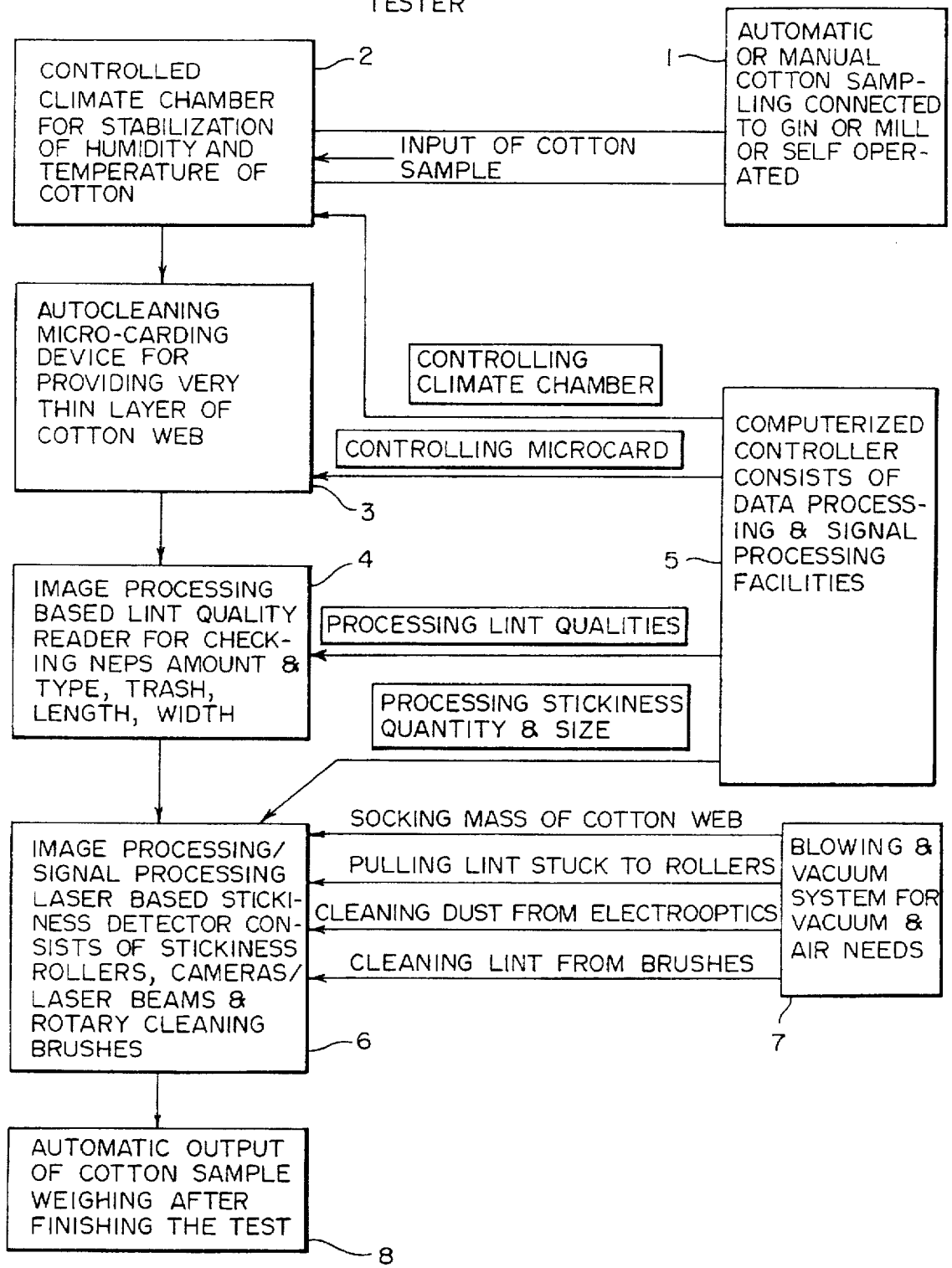

FIG. 1 explains the block diagram of the system according to the present invention. The automatic or manual cotton sampler (1) represents the existing industry such as cotton gin or mill or cotton classifying center which has an automatic or other sampler for feeding said invention system. During the modern ginning or milling process, the cotton is automatically sampled in each 10 second period by a pneumatic system. In said invention the cotton is transferred by vacuum to a controlled climate chamber (2). If no automatic sampler exists, it can be sampled manually. This is made for standardization of climate conditions such as precise humidity and precise temperature which are necessary for international standardization and for exposing sticky deposits to maximum sticky conditions and the fibers standard condition for quality classifying.

After spending sufficient and exact period of time in this chamber, the raw cotton is electronically weighed and sent to the bundle making device and sent to the microcarding device (3).

The main goal of the microcarding device is to make a thin layer of cotton web (approximately 10–30µ–10 mm) for maximum exposure of the sticky deposits and the neps, trash seed coat fragments and for other quality tests and contaminates. It consists of some saw covered rollers moving in different directions.

After finishing the carding process, the thin layer cotton web still consists of sticky deposits, neps, trash, seed coat fragments etc. which are not removed by the carding device. At this stage the cotton web falls in to the quality reader device (4). The quality reader device is a unit consisting of a video camera and illuminating means, an optional magnifying lens, and a black and white or colored gridded background. The web passes among the background and the camera and the data is sent to the computer controller and the processing unit (5) which is also used for the stickiness reader.

The computerized processing unit (5), sampling the data of the passing web at least 30 times in a second checking, by new statistical algorithm, the average width of the lint and the picture converting the microneer (an international cotton standard) data (or not) and compared to microneer standards. The typical color compared to international standards is also checked as is the number and characteristic neps for known area and weight. The amount of trash seed coat fragments or other contaminates in the web is also checked at this point.

Another part of the electro-optic system is the camera/laser unit which provides another algorithm for the stickiness test which process the number and size of points that were stuck to the stickiness rollers, the area and/or the electronic signal of which this lint was taken and also forecasts the probability that this cotton will cause sticky problems in the spinning mill.

After passing through the quality reader device, the cotton web falls in to the stickiness detector (6) which consists of main stickiness rollers which are pressed for insuring maximum contact between the rollers and the sticky deposits. The rollers are working in opposite directions and the web is slightly pulled by the vacuum system. While pressing the web between the rollers, the sticky deposits sticks some cotton lint which remains on the stickiness rollers in spits of the pulling of the cotton web (the force of the sticky deposits is greater) by the vacuum. The sticky lint on the rollers is detected by a stickiness checking laser beam device (FIG. 4a) or a video camera (line c.c.d. or other) (FIG. 4b) which is also connected to image processing unit in the computer (in case of video camera) (5). The lint passes through the stickiness camera sight. A dark background is used for better contrast. Illumination should be between the camera and the stickiness rollers. In the case of using laser beams or other sources of illuminating rays, the lint cuts the ray and the information effects the electronic photodetector sensor.

For recycling the process, the stickiness rollers, after the detection of the stickiness camera or laser, must be cleaned which is done by rotary brushes which rotate at much greater speed than the stickiness rollers. Static means can also be used for the same purpose. This cleaning can also include liquids and dry materials as necessary.

The blowing and vacuum system (7) connects to four different places and functions to:
1. slightly pull the cotton web;
2. Clean the rotary brushes from lint which is stuck on it after the electro-optic stickiness detection;
3. Clean dust from the electro-optic devices;
4. Very slightly pull the stuck lint for a better look at the stickiness by the electro-optic system and for checking the adhesive force of the sticky deposits. If the adhesive force is not high, the lint will be sucked by the vacuum. After the web passes all detection sites as mentioned above the web is automatically weighed and is removed from the tester (8).

Figure 2:
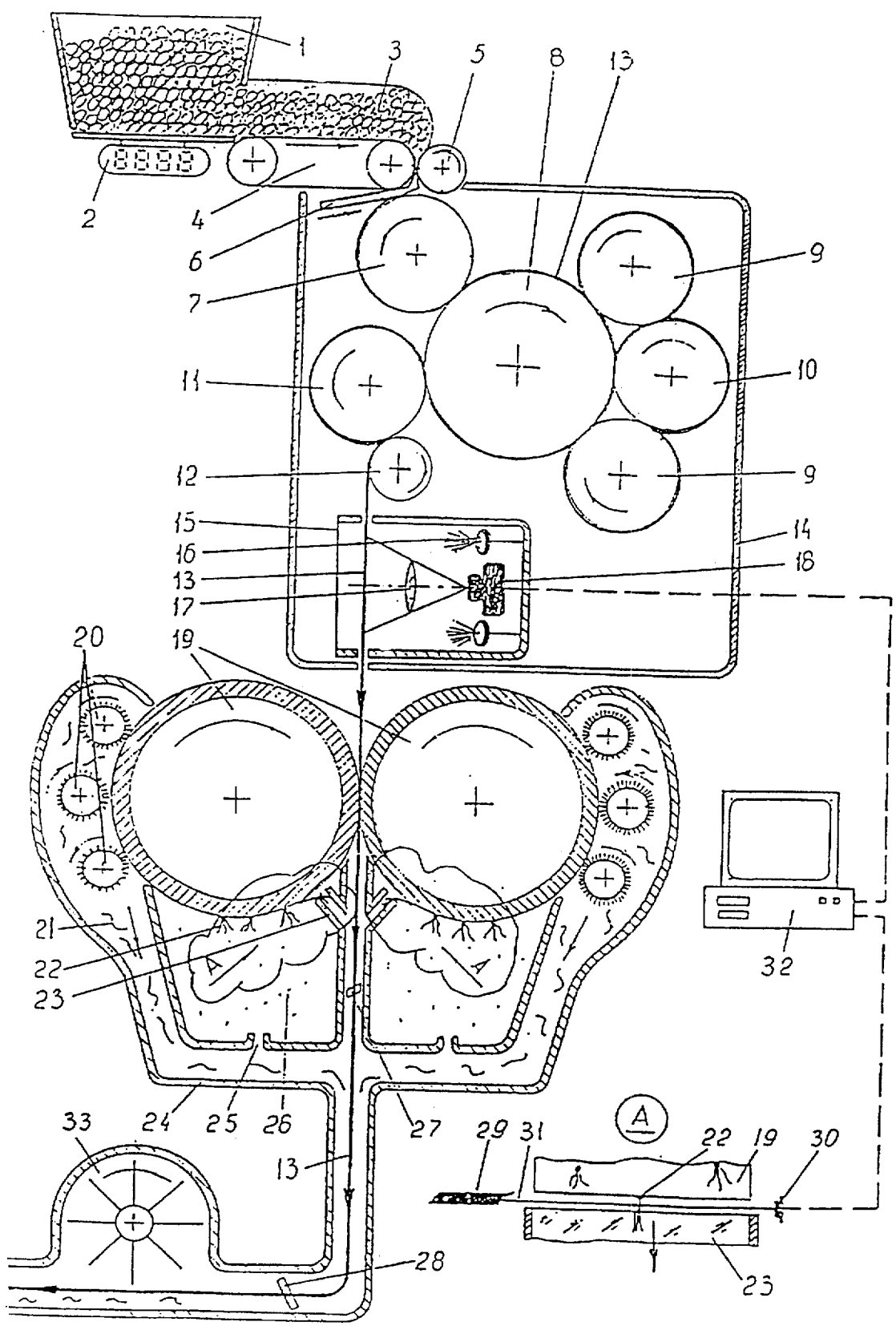
FIG. 2 illustrates a schematic view of the system according to the invention.

FIG. 2 represents the schematic drawing of the system according to the invention. During the ginning or milling process, or by manual operation, the cotton is automatically or manually sampled every number of seconds by a manual or pneumatic system and, transferred by vacuum to a controlled climate chamber (1) for standard climate conditions (such as humidity and temperature) which are necessary for international standardization and for exposing sticky deposits to maximum sticky conditions.

After spending a specific time in this chamber, the raw cotton (3) is automatically electronically weighed (2) and sent to a belt or other conveyor (4) which transfers the cotton to the feeding rollers (5) of the microcarding device, hereinafter called the "microcard".

The main goal of the microcard (7–12) is to make a thin layer of cotton web (approximately 10–30µ–10 mm) by combing for maximum exposure of the sticky deposits and exposing the amount of the cotton trash seed coat fragments, neps, and foreign material. The cotton web (13) first passes through a "lickerin" (7), a saw tooth covered roller, then to the main cylinder (8) which moves in different directions and speeds. The web then combed by the 3 rollers with lower speeds (9–10) and passes to the doffer (11). The web (13) then is removed by the take-off-roll (12) or a linear vibration device. After the microcard finishes this carding process, the thin layer cotton web (13) still consists of the sticky deposits, trash seed coat fragments material and neps which is not removed by the carding process. The carding rollers (9, 10) cleans the main cylinder automatically so no sticky deposits remain inside the microcard. The microcard consists of two carding sites (between rollers 9 and 8) for better carding. The cotton web (13), then falls into a Quality Reader device hereinafter called "Q.R.D." (15–18). The parts 5–18 are closed in a box (14).

The Q.R.D. is a unit consisting of a video camera (18) and illumination means (16), an optional magnifying lens or not (17), and a dark or white or colored and gridded background (15). The cotton web (13) passes between the background (15) and the camera (18) and the data is sent to the computerized image and signal processing unit hereinafter called "C.I.S.P.U." (32).

The C.I.S.P.U. (32) detects the passing web (13) approximately 30 times per second checking, by new statistical algorithm, the average width of the lint. The picture data converts to microneer (an international cotton standard) data, or not, and compares to microneer standards. The typical color compared to international standards is also checked and the number and size of neps of a known area and/or weight. The trash seed coat fragments and other foreign material remaining in the cotton web is also checked by the same image processing system but by opposite contrasts or other illumination means.

After passing through the Q.R.D., the cotton web (13) falls into two main stickiness roller (19) which are pressed one to the other, for insuring maximum contact between the rollers and the sticky deposits. The rollers (19) are working in opposite directions and the web (13) is slightly pulled by the vacuum system (33), then weighed and sent to waste or packing. While pressing the web (13) between the stickiness rollers (19) the sticky deposits sticks some cotton lint (22) which remain on the rollers (19) in spite of the pulling of the cotton web (13) (the force of the sticky deposits is greater) by the vacuum system (33).

The sticky lint (22) on the stickiness roller (19) are detected by at least one stickiness checking of laser beam or other illumination source (31) and detection device (30) (see also FIG. 4a) or video camera (line c.c.d or similar) (see also FIG. 4b) hereinafter called "electro-optic source" or "ES" (29) which is also connected to the C.I.S.P.U. in the computer (32).

The lint (22), after sticking to the stickiness roller (19) passes through the ES ray (31). The signal obtained from the photodetector (30) is correlated to the amount of lint which passed across the ES ray (31). In case of c.c.d. the illumination (FIG. 4b-35) should be between the camera (39) and the stickiness rollers (19). If the video camera is used for detecting the lint (22) on stickiness rollers (19) the lint must pass between the camera and the background (34).

For recycling of the process, the stickiness rollers (19), after the detection of the ES (31) should be cleaned, which is done by rotary brushes (20) which rotates at much greater speed than the stickiness rollers (19) or other means. This cleaning can also be done by other means including liquids and drying means as necessary. The cleaning can also be done by a nonend strip which would be pressed between the stickiness rollers.

The ES and/or the photodetector (30) provides data to the C.R.S.P.U., which is in the computer (32) which has an algorithm (enclosed as FIG. 5) for the stickiness data processing and processes the number and the size of cotton sticky deposits which were stuck to the stickiness rollers (19) as well as calculating the area or the signal height of which this lint was taken and also provides a forecast for the probability the cotton has of causing sticky problems in the cotton spinning mill.

The vacuum system (33) connects to four different places and functions to:
1. slightly pull the cotton web (13) after exiting from the stickiness rollers (19).
2. Pulling the lint (22) at precisely higher than the cotton grappling force and lower than adhesive to roller for checking the adhesive force of the lint (22) stack to the stickiness roller (19). This force depends on the amount of vacuum obtained from the nozzle (23). With more vacuum, less lint (22) will remain on the roller (19) and with more vacuum, there will be more adhesion of the sticky deposit.
3. Clean the rotary brushes (20) from lint (21) which stuck to it while cleaning the stickiness rollers (19), after the stickiness detection.
4. Clean dust (26) from the electro optical devices (29–30) by the air nozzle (25). An air regulator (27, 28) is installed inside or outside the pipes which pulls the cotton web (13) for regulating the very slight pull of the lint (22) on the stickiness rollers (19).

(The same system of stickiness rollers, with larger parts (consisting of parts numbers 19, 20, 21, 22, 24, 28, 33, 36, 37, and 38 (see also FIG. 3)) can be used in the gin for mass removal of stickiness from cotton (see also FIG. 6).

Figure 3:
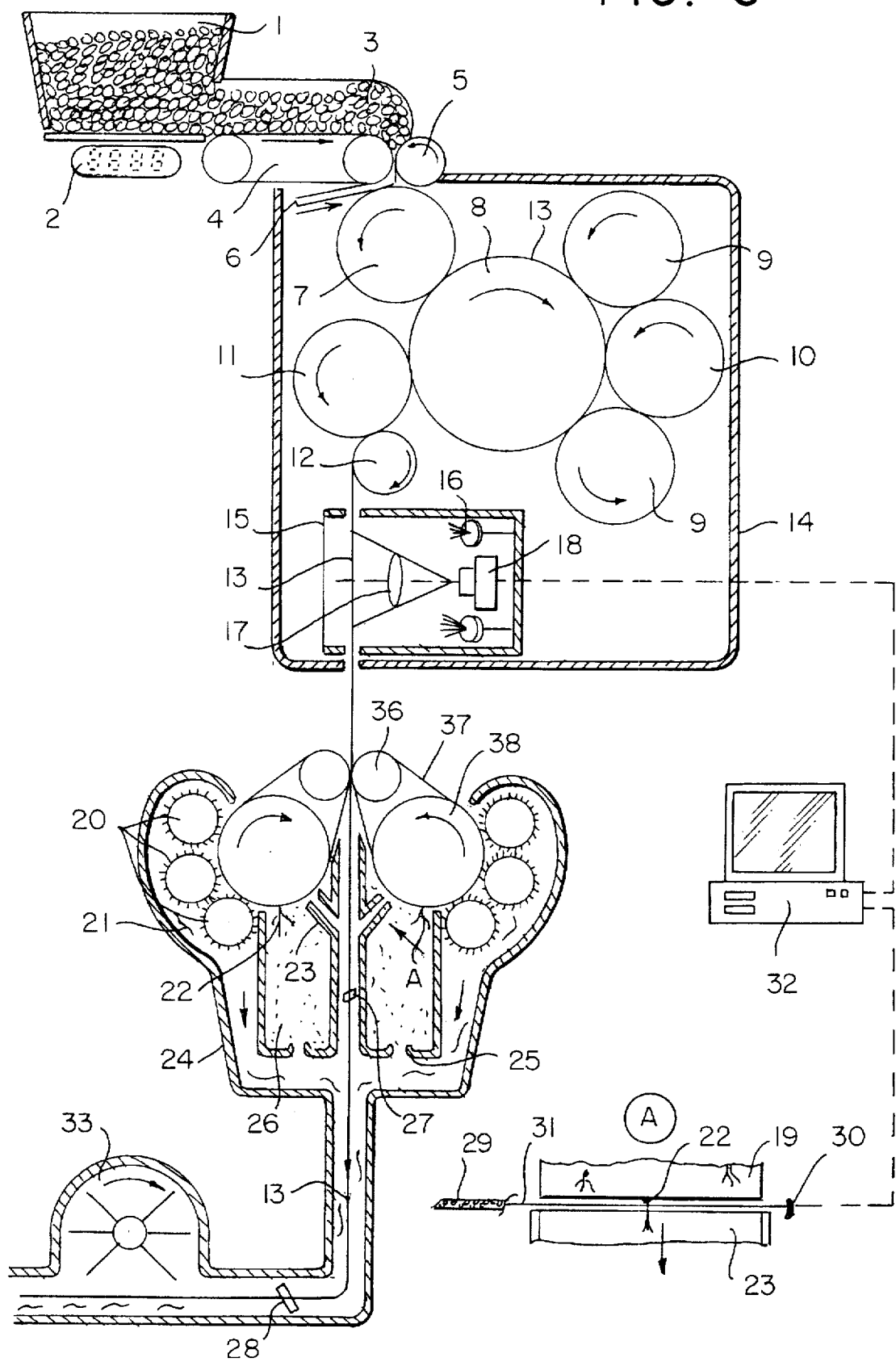
FIG. 3 illustrates another version of stickiness rollers (parts 36, 37, 38) as substitute to part 19 in FIG. 2.

FIG. 3 illustrates the same system with another version as a substitute to the stickiness rollers (19). This version consists of a metal belt (37) and stickiness rollers (36) and a cleaning roller (38). In this version the sticky deposits stick to the metal belt (37) instead of sticking to the stickiness roller (19) in FIG. 2.

FIG. 4 illustrates a magnification of two versions of the electro-optical system. In FIG. 4a an illumination device (29) (such as laser beam or other) is installed at the side and tangent site of the stickiness roller (19). The sticky deposits (22) which stuck to the roller which consists of the same lint is pulled by the vacuum which is in the nozzle (23). The vacuum straightens the lint and takes off the less adhesive deposits. The illumination source (29) and its detector (30) detects the lint (22), only when it is in the exit site of the nozzle and while it was fixed on the nozzle wall.

Version B is represented in FIG. 4b. In this version a c.c.d. camera (39) is installed at portrait site of the stickiness roller (19) enabling the system to detect more than one deposit at the same time and also to see this picture on the screen. For better detection, a dark background (34) should be placed behind the lint (22), and the illumination means (35) should be installed beneath the camera for better emphasis of the sticky deposits.

FIG. 5 represents a basic flow chart for the stickiness detection which is based on a laser beam version and outputs the total number of sticky deposits and its size.

FIG. 6a represents the metal belt cleaning of stickiness version, for the ginning site. This version consists of the stickiness rollers (36) for better contact between the sticky deposits and the metal belt. (See also FIG. 3—parts 36, 37, 38) Instead of the web, the raw cotton after the ginning (1) is passed between the two metal belts (37) which is pressed by the rollers (36) and then the cleaned raw cotton is sucked by a vacuum (33) pressing the sticky deposits sticks to the belt and are removed by the cleaning brushes (20) which are cleaned by a liquid or air stream.

FIG. 6b represents the same system as 6a but instead of using the metal belt, the system uses stickiness rollers (19) and brushes (20).

I claim:

1. A process for detection of stickiness, and at least one of neps, trash, seed coat fragments, length, width, color, and contaminants of cotton fibers, comprising:

producing a thin cotton web by means of a microcarding device by pressing the cotton web between rollers;

determining the number and size of at least one of neps, trash, seed coat fragments, length, width, color and contaminants by means of a camera;

pressing the thin cotton web produced in said microcarding device in a lint sticking device selected from the group consisting of two stickiness rollers which are pressed one onto the other, and rollers and belts wherein the belts are pressed one onto the other;

pulling said thin cotton web and any lint material through said stickiness rollers or belts in a vacuum system while detecting the stickiness of the cotton by at least one stickiness detector by determining the amount and character of the cotton lint adhering on said stickiness roller or belt to produce data;

inputting and processing the determined data in a computer system to determine the stickiness as well as at least one of length, width, color, trash, and contaminants in the cotton lint; and cleaning the stickiness rollers or belts.

2. The process of claim 1, wherein the stickiness detector comprises on one side of the stickiness roller or belt an illumination device for an electro-optic means for determining stickiness which projects tangentially to said stickiness roller or belt, and a photodectection device on the other side.

3. The process of claim 2, wherein the electro-optic means is selected from the group consisting of a laser beam, video camera, line camera, and a CCD camera.

4. The process of claim 1, wherein the computer system provides the information on at least one of the total sticky deposits, stickiness index, and contaminants per unit as numerical values with an optional graphic representation after a statistical analysis of data.

5. The process of claim 1, wherein the camera can detect at least one of color, width, average length of the cotton fiber, amount of neps, contaminants, and seed coat fragments within the thin cotton web after the microcarding process in real time.

6. The process claim 1, wherein said camera is selected from the group consisting of a video camera, IR camera, UV camera, and line camera.

7. The process of claim 1, wherein the camera is located between the microcarding device and the stickiness rollers.

8. The process of claim 1, wherein the camera is located after the stickiness rollers.

9. The process of claim 1, wherein at least one CCD camera is located behind the stickiness rollers and records the presence of sticky lint by detecting more than one deposit at the same time.

10. The process according to claim 1, wherein the stickiness rollers are cleaned by means of brushes, airstream, high vacuum, and liquid wetting and drying either independently or in a combination thereof.

11. A method for detection of stickiness, and at least one of neps, trash, and seed coat fragments, contaminants, length, width, color, and contaminants of cotton fibers, comprising:

taking samples of cotton before, during, or after the ginning or milling process;

preparing said samples for carding;

producing a thin cotton web of said samples by means of microcarding;

determining at least one of the number and size of neps, trash, seed coat fragments, length, width, color, and contaminants by means of a camera;

pressing the thin cotton web between rollers or belts;

pulling the web through said rollers or belts in a vacuum system while detecting the stickiness of the cotton by determining the amount and character of the cotton lint adhering on said roller or belt to produce data;

inputting and processing the determined data in a computer system; and cleaning the stickiness roller.

12. An apparatus for detection of stickiness, and at least one of neps, trash, seed coat fragments, length, width, color, and contaminants of cotton fibers, comprising:

means for producing a thin cotton web by means of a microcarding device by pressing the cotton between rollers;

means for determining at least one of the number and size of neps, trash, seed coat fragments, length, width, color, and contaminants by means of a camera;

means for pressing the thin cotton web produced in said microcarding device in a lint sticking device selected from the group consisting of two stickiness rollers which are pressed one onto the other, and rollers and belts wherein the belts are pressed one onto another;

means for pulling said thin cotton web and any lint material through said stickiness rollers or belts in a vacuum system while detecting the stickiness of the cotton by at least one stickiness detector by determining the amount and character of cotton lint adhering on said stickiness roller or belt to produce data;

means for inputting and processing the determined data in a computer system to determine the stickiness and at least one of the length, width, color, and contaminants in the cotton lint; and means for cleaning the said stickiness rollers or belts.

13. Process of claim 1, wherein said vacuum system pulls the cotton lint adhering on said stickiness roller so that said cotton lint stands vertically from the stickiness rollers or belts for detection by said stickiness detector.

14. Process of claim 11, wherein said vacuum system pulls the cotton lint adhering on said stickiness roller so that said cotton lint stands vertically from the stickiness rollers or belts for detection by said stickiness detector.

15. The process of claim 1, wherein at least one said stickiness detector is arranged to scan frontally the surface of the stickiness rollers.

* * * * *